United States Patent [19]

Taylor et al.

[11] Patent Number: 4,690,935

[45] Date of Patent: Sep. 1, 1987

[54] INHIBITION OF TUMOR GROWTH AND METASTASIS WITH CALCIUM CHANNEL BLOCKER COMPOUNDS

[75] Inventors: John D. Taylor, Detroit; Kenneth V. Honn, Grosse Pointe Woods, both of Mich.

[73] Assignee: Wayne State University, Detroit, Mich.

[21] Appl. No.: 480,704

[22] Filed: Mar. 31, 1983

[51] Int. Cl.$^4$ .................. A61K 31/44; A61K 31/55; A61K 31/495; A61K 31/275; A61K 31/125

[52] U.S. Cl. ............................. 514/356; 514/211; 514/255; 514/523; 514/654

[58] Field of Search .................... 424/263; 514/356

[56] References Cited

FOREIGN PATENT DOCUMENTS 2018134 of 0000 United Kingdom .

OTHER PUBLICATIONS

Chemical Abstracts 97:156177b, (1982).
Chemical Abstracts 99:205750k, (1983).
Weiss, L. In: Fundamental Aspects of Metastasis, pp. 1-5, 1976.
Fidler, I. J., Methods Cancer Res., 25:399-439, 1978.
Clark, R. L., Cancer 43:790-797, 1979.
Gordon, J. L. In: Platelets in Biology and Pathology-2. J. L. Gordon, ed., Elsevier North Holland Biomedical Press Amsterdam, pp. 1-7, 1981.
Weiss, H. J. In: Platelets: Pathophysiology and Antiplatelet Drug Therapy, Alan R. Liss, Inc., New York, pp. 13-17, 1982.
Jamieson, G. A., Bastida, E. and Ordinas, A. In: Interaction of Platelets and Tumor Cells, G. A. Jamieson, ed., Alan R. Liss Inc., New York, pp. 405-413.
Gasic, G. J., Gasic, T., Galanti, N., Johnson, T. and Murphy, S., int. J. Cancer 11:704-718, 1973.
Hara, H., Steiner, M. and Baldini, M. G., Cancer Res. 40:1217-1222, 1980.
Bastida, E., Ordinas, A. and Jamieson, G. A., Nature 291:661-662, 1981.
Gasic, G. J., Gasic T. B. and Steward, C. C., Proc. Natl. Acad. Sci. USA 61:46-52, 1968.
Honn, K. V., Cicone, B. And Skoff, A., Science 212:1270-1272, 1981.
Menter, D., Neagos, G., Dunn, J., Palazoo, R., Tchen, T. T., Taylor, J. D. and Honn, K. V. In: Prostaglandins and Cancer, First Intl. Conf., pp. 809-813, 1982.
Mustard, J. F. and Packham, M. A. Pharmac. Rev. 22:97-187, 1970.
Mills, D. C. and MacFarlane, D. E. In: Platelets in Biology and J. L. Gordon, ed., North Holland Press, New York, pp. 159-163, 1976.
Meyers, K. M., Seachord, C. L., Holmsen, H., Smith, J. B. and Prieur, D. J., Nature 282:313-333, 1979.
Shaw, J. O. and Lyons, R. M., Biochem. Biophys., Acta 714:492-499, 1982.
Imai, A., Kawai, K. and Nozawa, Y., Biochem. Biophys. Res. Commun., 108:(2) 752-759, 1982.
Kao, K. J., Sommer, J. R. and Pizzo, S. V., Nature 292:(5818) 82-84, 1981.
Gerrard, J. M., Peterson, D. A. and White, J. G. In: Platelets in Biology and Pathology-2, J. L. Gordon, ed., North Holland Biomedical Press, Amsterdam, pp. 407-436, 1981.
Rittenhouse-Simmons, S. L. Biol. Chem., 256:(9) 4153-4155, 1981.
Shukla, S. D., Life Sciences 30:1323-1335, 1982.
Serhan, C. N., Fridovish, J., Goetzel, E. J., Dunham, P. B. and Weissman, G. J., Biol. Chem. 257:(9) 4746-4752, 1982.
Gorman, R. R., Fed. Proc. 38:(1) 83-88, 1979.
Parise, L. V., Venton, D. L. and Ledreton, G. D., J. Pharm. Exptl. Therap. 222:(1) 276-281, 1982.
Circulation 62, (Suppli. III, Abstracts No. 1123,1258), abstract of 53rd Scientific Session 62, Suppli. III, Oct. 1980.
Fleckenstein A., An. Rev. Pharmacal. Toxical 17:149-166, (1977).
Exptl. Cell Res., 13:341-347, (1957).
Anal. Biochem. 98:112-115, (1979).
Diglio, C. A., Grammas, P., Giacomelli, F., and Wiener, J., Lab. Investigations, vol. 46, No. 6, pp. 554-563, 1982.
Diglio, C., Wolfe, D. E., and Meyers, P. J. Cell. Biol. Manuscript in press, 1983.

Primary Examiner—Jerome D. Goldberg
Attorney, Agent, or Firm—Ian C. McLeod

[57] ABSTRACT

The use of calcium channel blocker compounds as antitumor and antimetastatic agents in mammals in vivo and in standard laboratory experimets with tumor cells in vitro is described. In particular the use of nimodipine (Bay e 9736) or nifedipine (Bay a 1040) and structurally related compounds as described.

7 Claims, No Drawings

INHIBITION OF TUMOR GROWTH AND METASTASIS WITH CALCIUM CHANNEL BLOCKER COMPOUNDS

BACKGROUND OF THE INVENTION

(1) Field of the Invention

The present invention relates to the use of calcium channel blocker compounds, known for use in the treatment of cardiovascular disorders, such as hypertension, angina and arrhythmia, for the inhibition of tumor growth and metastasis. In particular, the present invention preferably relates to the use of nimodipine (BAY e 9736) and nifedepine (Bay a 1040) and structurally related compounds for such inhibition; however, many other calcium channel blocker compounds can be used.

(2) Prior Art

The primary focus of cancer therapy and research has been directed towards the treatment of the initial or primary tumor. Considerable success has been achieved by utilizing surgery, radiotherapy, and/or chemotherapy. However, it has become increasingly apparent that metastasis, the spread of cancer from the initial tumor to other physically separate sites in the body, is an equally life-threatening situation that must be confronted. The exact steps of metastasis are not known, but it has been proposed, and to a certain extent demonstrated, that the entrapment or adhesion of loosened tumor cells of the primary tumor circulating in the vasculatory or lymphatic systems to endothelial substrate in the systems may be an important step of the metastatic cascade.

The metastatic cascade can be described as a sequence of events, that a tumor cell or cells must successfully complete in order to become a metastatic foci. Although different authors vary somewhat in their terminology, the cascade can be thought of as four sequential stages or steps (Weiss, L. In: Fundamental Aspects of Metastasis. pp. 1–5, 1976; Fidler, I. J., Methods Cancer Res. 25:399–439, 1978; and Clark, R. L. Cancer 43:790–797, 1979). First, a tumor cell or clump of tumor cells must be "shed" by the primary tumor. Second, the tumor cells must enter the vascular or lymphatic system and avoid destruction by host immune defenses (macrophages, natural killer cells, immune complexes, etc.). Third, the tumor cells must adhere to the endothelial lining of the vascular or lymphatic system. Fourth, the adhering tumor cells must avoid dislodgement, extravasate through the endothelium and divide. Tumor cell interactions with host platelets to form a tumor cell-platelet aggregate or thrombus has been proposed as a possible mechanism that would allow tumor cells to successfully complete the last stages of the metastatic cascade.

Platelet aggregation and adhesion are typically thought to be initiated by a number of soluble and non-soluble factors including catecholamines, prostaglandins, immune complexes, complement components, ADP, and collagen (Gordon, J. L. In: Platelets in Biology and Pathology - 2. J. L. Gordon, ed., Elsevier North Holland Biomedical Press, Amsterdam, pp. 1–7, 1981; Weiss, H. J. In: Platelets: Pathophysiology and Antiplatelet Drug Therapy. Alan R. Liss, Inc., New York pp. 13–17, 1982; and Jamieson, G. A., Bastida, E. and Ordinas, A. In: Interaction of Platelets and Tumor Cells. G. A. Jamieson, ed., Alan R. Liss, Inc., New York, pp. 405–413). Additionally, it has been demonstrated that tumor cells can induce platelet aggregation (Gasic, G. J., Gasic, T., Galanti, N., Johnson, T. and Murphy, S. Int. J. Cancer 11:704–718, 1973; Hara, H., Steiner, M. and Baldini, M. G. Cancer Res. 40:1217–1222, 1980; and Bastida, E., Ordinas, A. and Jamieson, G. A. Nature 291-: 661–662, 1981). It is possible that the resultant tumor cell-platelet thrombus could protect or shield the tumor cells from attack by the host immune system, increase the likelihood that the tumor cells would adhere to the endothelial lining of the vascular system, and protect adhering tumor cells from dislodgement. Thus, pharmacological agents that inhibit platelet aggregation or reduce platelet number have been investigated for their ability to suppress metastasis (Gasic, G. J., Gasic, T. B. and Steward, C. C. Proc. Natl. Acad. Sci. USA 61:46–52, 1968; Honn, K. V., Cicone, B. and Skoff, A. Science 212:1270–1272, 1981; and Menter, D., Neagos, G., Dunn, J., Palazoo, R., Tchen, T. T., Taylor, J. D. and Honn, K. V. In: Prostaglandins and Cancer. First Intl. Conf., pp. 809–813, 1982).

Platelet aggregation is usually thought of as a sequential process involving "primary" platelet aggregation, which consists of the direct interaction of an aggregating agent with its specific receptor on the platelet surface (Mustard, J. F. and Rackham, M. A. Pharmac. Rev. 22:97–107, 1970; and Mills, D. C. and MacFarlane, D. E. In: Platelets in Biology and Pathology. J. L. Gordon, ed., North Holland Press, New York, pp. 159–163, 1976), and "secondary" platelet aggregation which may involve the release of storage granules and the influx of extracellular calcium (Meyers, K. M., Seachord, C. L., Holmsen, H., Smith, J. B. and Prieur, D. J. Nature 282:331–333, 1979; Shaw, J. O. and Lyons, R. M. Biochim. Biophys. Acta 714:492–499, 1982; and Imai, A., Kawai, K. and Nozawa, Y. Biochem. Biophys. Res. Commun. 108:(2)752–759, 1982). While there is still some debate as to the specific platelet processes involved in primary as opposed to secondary platelet aggregation, an intraplatelet increase in calcium ion ($Ca^{++}$) and an influx of extracellular calcium are definitely involved in platelet aggregation, and perhaps even serve as triggering mechanisms (Kao, K. J., Sommer, J. R. and Pizzo, S. V. Nature 292:(5818)82–84, 1981; Gerrard, J. M., Peterson, D. A. and White, J. G. In: Platelets in Biology and Pathology - 2. J. L. Gordon, ed., North Holland Biomedical Press, Amsterdam, pp. 407–436, 1981: Rittenhouse-Simmons, S. J. Biol. Chem. 256:(9)4153–4155, 1981; Shukla, S. D. Life Sciences 30:1323–1335, 1982; Serhan, C. N., Fridovish, J., Goetzel, E. J., Dunham, P. B. and Weissman, G. J. Biol. Chem. 257:(9)4746–4752, 1982; Gorman, R. R. Fed. Proc. 38:(1)83–88, 1979; and Parise, L. V., Venton, D. L. and Lebreton, G. D. J. Pharm. Exptl. Therap. 222:(1)276–281, 1982). Thus, the recent reports that calcium channel blockers can inhibit platelet aggregation induced by ADP or epinephrine are not surprising. Circulation 62 (Suppl. III Abstracts No. 1123, 1258) Abstract of 53rd Scientific Sessions 62 Suppl III October 1980.

Calcium ions function as extracellular and intracellular messengers and regulating agents to control myriad physiological functions. The control of platelet aggregation is only one small regulatory function of calcium. Clinically, one of the most important functions is its regulation of muscle contraction. Within the past two decades the concept has developed that the blocking of calcium effects could be clinically useful in the treatment of disorders resulting from restricted blood flow (through vascular, pulmonary, and/or coronary arteries) and from arrhythmias (abnormalities in the contractions of the heart).

An increase in intracellular $Ca^{++}$ triggers contraction in both the smooth muscle tissue of the arteries and the cardiac muscle tissue of the heart. In both types of muscle tissue, the entry of $Ca^{++}$ triggers interactions between two proteins, actin and myosin, leading to cellular contraction, and is responsible for the contractions of the heart and the diameter and flow rate of blood through arteries. Although the muscle cells of the heart and arteries contain structures which store and release $Ca^{++}$, it is the entry of $Ca^{++}$ from outside the muscle cells through selective sites in the cell membrane, the so-called "calcium channels," which trigger muscle contraction. Because of selective imbalances in positively and negatively charged ions between the inside and the outside of all cells of the body, there exists an electrical charge difference, measurable in millivolts across living cell membranes, including muscle cell membranes. The calcium channels are normally closed in the resting muscle cell, and open to permit the entry of $Ca^{++}$ into the muscle cells only during depolarization of the muscle cell membrane (i.e., a reversal of polarity across the muscle cell membrane).

Although there are structures in the muscle cell membrane that regulate the opening and closing of the calcium channel independent of depolarization, and certain ions such as manganese and cobalt can keep the calcium channels closed, these factors all are non-specific in that they affect other cellular functions.

Organic calcium channel blockers are highly specific and can exert their effects in nanomolar concentrations. The primary work of Fleckenstein A., Am. Rev. Pharmacol. Toxicol. 17:149–166 (1977) determined that these compounds could selectively blockade the calcium channels and electrical functions of muscle tissue. Calcium channel blockers may function by actually "plugging" the "closed" channel of the resting muscle cell membrane (nimodipine and nifedipine), or they may interact with the "open" calcium channel during depolarization (verapamil and diltiazem). The "open" channel blockers function best during muscular contraction.

A number of vascular and myocardial disorders can be alleviated by inducing vasodilation by calcium channel blocker treatment (i.e., relaxation of arterial smooth muscle which results in increased blood flow). These include: (1) vasospastic angina, including Prenzmetal's angina; (2) stable (effort-induced) angina; (3) acute myocardial infraction; (4) surgically induced myocardial arrest; (5) arrhythmias; (6) systemic hypertension; (7) pulmonary hypertension; (8) congestive heart failure; (9) hypertrophic cardiomyopathy. All of these disorders have in common a decrease in blood flow or availability and as a common relief, an increase or easing of blood flow which can be induced by the vasodilating effects of calcium channel blockers.

Many compounds are known to function as an antimetastatic agent using different mechanisms for interrupting the metastatic cascade. We, as well as others, have proposed and demonstrated that tumor metastasis is enhanced by tumor cell interactions with platelets and that agents which block or prevent tumor cell-platelet interaction and aggregation have antimetastatic effects. Agents which have been investigated function by reducing platelet cell number in the blood or by inhibiting platelet function (aggregation). Pending U.S. patent application Ser. No. 420,642, filed Sept. 21, 1982 by one of the inventors herein jointly with others describes nafazatrom, an anticoagulant, which is used as an antitumor and antimetastatic agent.

Objects

It is therefore an object of the present invention to provide calcium channel blocker compounds known for use in the treatment of cardiovascular disorders which inhibit metastasis in mammals. These and other objects will become apparent by reference to the following description.

General Description

The present invention relates to a therapeutic method for reducing metastasis and neoplastic growth in a mammal which comprises administering a therapeutically effective amount of a calcium channel blocker compound or a pharmaceutically acceptable acid addition salt thereof. The compounds have the ability to inhibit tumor cell induced platelet aggregation in vitro which is related to in vivo activity. The present invention particularly relates to a method wherein the calcium channel blocker compound is nimodipine (BAY e 9736) which is 1,4-dihydro-2,6-dimethyl-4-(3' nitrophenyl)-pyridine-3-(beta-methyoxyethyl ester)-5-(isopropyl ester). It is described in British Patent application No. 2,018,134. Another preferred channel blocker compound is nifedipine (BAY a 1040) which is 4-(2'-nitrophenyl-2,6-dimethyl-1,4-dihydropyridine. The calcium channel blocker compounds include the 1-unsubstituted and 1-substituted 1,4,di-hydropyridine compounds described in British Pat. No. 1,430,961 which are substituted in the 4-position and which are vascular dilators. Nifedipine and nimodipine are of the class of 1,4-dihydro-2,6-dimethyl-4-(3'nitrophenyl)-pyridine-3-(lower alkyl ester)-5-(lower alkyl ester), wherein lower alkyl is between 1 to 6 carbon atoms which can be straight chain or branched. Felodipine is a potent new compound which is being developed in Sweden in the 1,4-dihydropyridine class.

Also included as calcium blocker vasodilator compounds are verapamil and diltiazem and related compounds which are described in the Merck Index, 8th Edition. These compounds are structurally unrelated to the 1,4-hydropyridine compounds but are believed to also inhibit platelet aggregation. Verapamil is in the class of phenyl alkylamines and diltiazem is in the class of benzothiapenes as channel blocker compounds. Other calcium blockers are prenylamine and lidoflazine which are in the class of diphenylalkylamines. There are many compounds in each class and all are well known to those skilled in the art.

The present invention also relates to a method for testing for the prevention of tumor cell induced platelet aggregation which comprises incorporating in vitro with selected platelets and tumor cells which aggregate an effective amount of a calcium channel blocker vasodilator compound or a pharmaceutically acceptable acid addition salt thereof to test the compound for inhibition of platelet aggregation with the selected tumor cells. Thus using this method it can be determined whether a selected tumor cells-platelet combination from a particular mammal will be responsive to treatment with the calcium channel blocker compound. This is an important test since not all tumor cells may be responsive to treatment with all calcium channel blocker compounds, particularly if additional primary tumor active compounds are to be used together with the calcium channel blocker compounds. Thus in living systems, the prevention of the metastatic cascade is more difficult to detect and continuous testing is required.

Drug Forms

The acid-addition or amine salts of the amine bases of the invention can be prepared by reacting the free base with a pharmaceutically-acceptable organic or inorganic acid. Some examples of the many pharmaceutically-acceptable organic and inorganic acids which can be used to produce the corresponding acid-addition salts are hydrochloric acid, hydrobromic acid, sulfuric acid, phosphoric acid, acetic acid, citric acid, tartaric acid, sulfamic acid and the like. The term "pharmaceutically-acceptable acid" designates an acid capable of being employed in the production of salts suitable for pharmaceutical use even though, like corrosive or strong mineral acids, it may not be acceptable for pharmaceutical use in and of itself. The term "salts" combined with the phrase "with pharmaceutically-acceptable organic or inorganic acid" in reference to the salts refers to chemical structure rather than to method of formation and includes such salts whether formed by neutralization or other salt forming means.

In the present specification the expression "diluent or carrier" means a pharmaceutically acceptable non-toxic substance that when mixed with the active ingredient or ingredients renders it suitable for administration. The expression preferably excludes water and low-molecular weight organic solvents commonly used in chemical synthesis, except in the presence of other pharmaceutically necessary ingredients such as salts in correct quantities to render the composition isotonic, buffers, surfactants, coloring and flavoring agents, and preservatives. Examples of suitable solid and liquid diluents and carriers are the following: water containing buffering agents which can be rendered isotonic by the addition of glucose or salts; non-toxic organic solvents; such as paraffins, vegetable oils; alcohols; glycols; natural ground rock (for example kaolins, aluminas, talc or chalk); synthetic rock powders (for example highly dispersed silica or silicates); and sugars.

Oral administration can be effected utilizing solid and liquid dosage unit forms such as powders, tablets, dragees, capsules, granulates, suspensions, solutions and the like. Where appropriate, dosage unit formulations for oral administration can be microencapsulated to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Stabilizers, preservatives and emulsifiers can also be added.

Generally the parenteral dosage will be from 0.01 to 50 mg/kg, preferably from 0.1 to 10 mg/kg, of body weight per day, and the oral dosage form will be from 0.1 to 500 mg/kg, preferably 0.5 to 100 mg/kg, of body weight per day.

Specific Description

Test Procedures

The composition for administration can contain between about 0.1 to 90% of the active ingredient of the composition. British application No. 2,018,134 describes various compositions of nimodipine (Bay e 3736).

The following procedure was used to determine the antimetastatic properties of nimodipine (BAY e 9736). The test protocol utilized two unrelated murine tumor type (a melanoma and a carcinoma) to minimize the possibility the results obtained are "unique" to a single tumor type. Both of these tumors are routinely used for basic studies on the mechanism of metastasis.

At present, there are two "model" systems widely used in studying in vivo metastasis. The first model system involves the subcutaneous injection of tumor cells into the animal. Subcutaneous injection of tumor cells and subsequent development of a primary tumor, followed by spontaneous metastasis is considered to be "full" metastasis. Another model system involves the injection of tumor cells via the tail vein. Considering the complexibility of metastasis, it is recognized that tail vein injection is an artificial and only partial model system, since it represents events occurring in the latter portion of metastasis. However, the tail vein model system is recognized as being extremely useful in standardizing experimental conditions (See *Methods in Cancer Research,* Chapter VII, Academic Press, Inc., 1978.)

The antimetastatic effects of BAY e 9736 (nimodipine) was tested in a number of different in vivo and in vitro assay systems. It was demonstrated that the chronic administration of nimodipine to mice will significantly reduce spontaneous metastasis and that prior treatment of nimodipine will reduce metastasis induced by tail vein injection of B16a tumor cells to syngeneic mice. In vitro, it was demonstrated that nimodipine will greatly inhibit platelet aggregation induced by tumor cells and ADP. We also demonstrated that nimodipine decreases the rate of tumor cell growth over a five day assay period, decreases the rate of incorporation of $^3$H-thymidine into tumor cell DNA, and decreases or inhibits the adhesion of tumor cells to plastic incubation wells and to virally transformed endothelial cell monolayers.

MATERIALS AND METHODS

In Vitro Maintenance of B16a Tumors

B16 amelanotic melanoma (B16a) and Walker 256 L-Pam carcinosarcoma were obtained from the Division of Cancer Treatment, Animal and Human Tumor Bank, Mason Research Institute, Worcester, Mass. Tumors were passaged four times after receipt in syngeneic C57BL/6J male mice (B16a) or allogenic Sprague Dawley rats (Walker 256 L-Pam). Passaging involved subcutaneous implantations of tumor pices (diced to approximately 2×2 MM) into the right auxiliary region using a 18 gauge needle. Mice weighing approximately 20 grams (4 to 5 weeks old) were used to passage the B16a cell line and female rats were used to passage the Walker 256 L-Pam cell line. Animals were housed under identical conditions of temperature, feeding, photoperiod, etc. The transplanted tumors were allowed to grow for approximately 14 days following implantation.

Platelet Rich Plasma Preparation

Blood (45 ml) was drawn from the anteorbital vein of healthy, fasted, aspirin free (at least two weeks) human volunteers into a plastic syringe containing 5 ml of 4.8% dextrose with 50 U/ml heparin buffered by 25 mM HEPES, pH 7.5. An 18 gauge needle was used to prevent hemolysis. The heparinized blood was gently mixed by inverting the syringe five times and then the blood was transfused into two 40 ml plastic centrifuge tubes and centrifuged for 10 min at $163 \times g$. The resulting platelet rich plasma (PRP; the supernatant fraction) was decanted using an adjustable SMI pipette set at 6 ml. Platelet poor plasma (PPP) was prepared by centrifugation of PRP for 10 min at $1086 \times g$. Platelet poor plasma was used to standardize the platelet concentration in PRP to $3 \times 10^8$/ml. Platelet concentrations were determined using a Coulter Model ZBI cell counter.

Preparation of Rat Platelets

Female rats were anesthetized with sodium pentobarbital (52 mg/kg) and bled via the renal vein. Approximately 10 ml of blood was collected from each rat via an 18 gauge needle into a syringe containing 1 milliliter of 3% sodium citrate. Rat platelet-rich plasma (PRP) was prepared as described in another section of this application (for human PRP) to a final concentration of $7.7 \times 10^8$ platelets/ml.

Measurement of Platelet Aggregation

Platelet aggregation was measured photometrically using a Sienco Model DP-247E dual channel aggregometer and recorded on a Sienco Model B-5000 dual channel recorder. Aliquots of PRP (250 microliters at $3 \times 10^8$ platelets/ml) were transferred into aggregometry cuvettes and stirred at a constant speed of 800 RPM at 37° C. Platelet aggregation studies were designed and run as individually controlled samples. BAY e 9736 was dissolved in either PEG-400 or dimethylsulfide (DMSO). Because no statistically significant differences were observed in preliminary aggregometry studies between BAY e 9736 dissolved in PEG-400 and DMSO on their effects on platelet aggregation, PEG-400 was utilized for the studies reported.

BAY e 9736 in PEG-400 alone was aliquoted into the cuvettes prior to the addition of the PRP. Immediately after the addition of the PRP, the cuvettes were placed into the aggregometer. After two minutes (to allow for the stabilization of the platelet preparation and mixing of the BAY e 9736), ADP or tumor cells were added in 20 microliter aliquots to induce platelet aggregation.

Dispersion and Elutriation of Tumor Cells

Subcutaneous B16a primary tumors were excised, diced and dispersed by collagenase digestion. Tumor pieces (4×4 mm) were divided in approximately 500 mg aliquots and placed in sterile polycarbonate flasks. Ten ml of TDS, "tumor dispersion solution," was added to each flask. TDS was prepared by mixing Composition A and Composition B described below.

| Composition A (based on 1 liter) | |
|---|---|
| 9.5 g/l | Sterile Eagles's Minimum Essential Medium (MEM), commercially available from GIBCO, Grand Island, New York |
| 10 ml/l | Non-essential Amino Acids (GIBCO) |
| 10 ml/l | Sodium pyruvate |
| 0.35 g/l | Sodium bicarbonate (15 mM) |
| 5.9 g/l | HEPES (25 mM0 an organic buffer; commercially available from Sigma Chemical Co., St. Louis, Missouri |
| 150 Units/ml | Penicillin |
| 100 μg/ml | Neomycin sulfate |

The antibiotics were added to ensure that bacterial contamination did not occur.

Composition B is a dry mixture containing collagenase low in clostripain and other proteolytic activity; deoxyribonuclease (DNase to dissolve deoxyribonucleoprotein released from damaged cell nuclei; lima bean or soybean trypsin inhibitors to exclude any residual tryptic activity; human serum albumin to eliminate nonspecific protease activity and absorb peroxy and hydroperoxy fatty acids liberated from damaged membranes.

| Composition B | Weight/ml Composition A |
|---|---|
| Collagenase (Worthington type III) | 1 mg/ml |
| DNase I (Sigma Chemical) | 70 μg/ml |
| Soybean trypsin inhibitor (Worthington) | 100 μg/ml |
| Human serum albumin (fatty acid-free; Sigma chemical) | 10 mg/ml |

Composition B was weighed out and placed in a flask and 100 ml of Composition A added.

The diced tissue in the TDS was then dispersed (15 min. 37°C.) under air in a Dubnoff Metabolic Shaker (90 oscillations/minute). Supernatants were collected through cheesecloth into sterile 50 ml polycarbonate round bottom centrifuge tubes and centrifuged for 10 minutes (25° C.) at 900 rpm ($100 \times g$) in a Sorvall SS-34 rotor. Following centrifugation, the supernatant fraction was discarded. The solid cellular matter (pellets) obtained were washed twice with MEM solution, resuspended in MEM and held at 4° C. (a 10 ml portion of TDS added to remaining diced tissue, incubated as above for 45 min, supernatants collected and treated as above).

A 10 ml portion of TDS was added to the remaining diced tissue and the tissue incubated in a metabolic shaker as described herein above, except for a period of 60 minutes. The centrifugation was repeated and the resuspended cells were combined.

The cell viability was determined by the vital dye exclusion method (see *Exptl. Cell Res.* 13: 314–347, 1957). The cell count was determined in a hemocytometer. The stromal cell contamination, e.g. macrophage, red blood cells, etc., was determined by visual examination under a microscope. The final cell suspension obtained consisted of greater than 99 percent monodispersed cells with approximately 25 percent host stromal cell contamination Typical yields from 6 grams of diced B16a tumor cells ranged between 3 to $7 \times 10^8$ dispersed tumor cells.

The final cell suspensions were then subjected to centrifugal elutriation for final separation of the tumor cell. In centrifugal elutriation, cells are subject to two opposing forces within a separation chamber; a centrifugal field generated by a spinning rotor and a counterflow of fluid in the opposite (centripetal) direction. A sample suspended in a medium enters the separation chamber. Each cell tends to migrate to a zone where its sedimentation rate is exactly balanced by the flow rate of the fluid through the separation chamber. The chamber's geometry produces a gradient of flow rates from one end to the other; cells with a wide range of different sedimentation rates can be held in suspension. By increasing the flow rate of the elutriating fluid (separation medium) in steps, or by decreasing the rotor speed, successive populations of relatively homogeneous cell sizes can be washed from the chamber. Each population will contain cells which are larger or more dense (i.e., faster sedimenting) than those of previous fractions.

Centrifugal elutriation was accomplished by suspending the tumor cells in a "Tumor Resuspension Solution" (TRS), Composition A alone. The suspension was elutriated using a Beckman JE-6 elutriator rotor operating at 1460 rpm in a Beckman J-2-21 centrifuge at 25° C.

A separation medium (Hank's Balanced Salt Solution, MEM or Composition A+0.01% albumin (for murine tumor cells) +0.1% albumin (for CLA tumor cells)) was pumped through the system using a Cole Palmer Master Flex pump with a No. 7014 pump head. The pump control box was modified with a 10 turn potentiometer (see *Anal. Biochem.* 98: 112–115, 1979). The flow rate was measured with a Brooks double-ball flow valve.

Approximately $5 \times 10^8$–$1 \times 10^9$ cells were injected through an in-line "Y" fitting into the mixing chamber. Cells were loaded into the separation chamber at flow rate of 6 ml/min. The "Y" position was changed so that only clean composition A would wash the cells which were then washed at speeds of 6, 9 and 12 ml/min, collecting 100 ml at each flow rate. These were discarded. Cells were collected at 15, 28, 40 and 52 ml/min fractions, 200 ml/fraction. These fractions were recentrifuged ($100 \times g \times 10$ min) and resuspended in 1 to 2 ml TRS.

Recoveries were generally between 70–75 percent of the cells injected into the mixing chamber. Viability determined as previously described. Cell numbers were determined using a Coulter counter (model ZBI; Coulter Electronics).

Proliferation Studies

Proliferation studies were designed to measure the effects of BAY e 9736 on the proliferation of B16 a tumor cells. B16a tumor cells were plated into T-25 flasks ($4 \times 10^4$ cells/flask) and allowed to grow at 37° C. for 16 hours. The media was removed from the flasks and plating efficiency was determined using a Coulter counter. Replacement media was added to the flasks, which were allowed to incubate for 24 hours. After the 24 hour incubation, 10 microliters of control (media), DMSO, or BAY e 9736 in DMSO (40 mg/ml stock) was added to the flasks. Media replacement with and without BAY e 9736 were performed every 24 hours for 4 consecutive days. Control flasks (3) were terminated every day of the proliferation study with 4 terminated on the final day.

$^3$H-Thymidine Incorporation Studies $^3$H-thymidine incorporation studies were designed to measure the effects of BAY e 9736, nimodipine on the incorporation of $^3$H-thymidine into the DNA of B16a tumor cells. One ml of cultured B16a tumor cells (in MEM+10% fetal calf serum) at $1 \times 10^5$ cells/ml are placed into plastic incubation tubes. The cells are incubated for 15 minutes at 37° C. in the presence of five microliters of diluent (DMSO, dimethyl sulfoxide) alone or diluent containing BAY e 9736. After 15 minutes, which is considered the preincubation period, the cells are incubated for one hour (at 37° C.) in the presence of one microcurie (per ml) $^3$H-thymidine. The assay is terminated by the addition of one milliliter of cold trichloroacetic acid, TCA, (6% w/v). The cells are centrifuged at $10,000 \times g \times 4$ minutes. The supernatant is discarded. The resulting pellet is resuspended in one milliliter of TCA, vortexed and then repelleted by centrifugation at $10,000 \times g \times 4$ minutes. The supernatant is discarded. The pellets are resuspended in 100 microliters of tissue solubilizing fluid (NCS from Amersham Corporation) and incubated for 2 hours at 50° C. Fifty microliter aliquots of the solubilized pellets are transferred into plastic scintillation vials containing 3 milliliters of scintillation fluid (Econofluor, New England Nuclear), allowed to cool and dark adjust, and counted.

Preparation of $^{125}$I Radiolabelled Tumor Cells

Walker $^{256}$ L-Pam tumor cells were plated at approximately $5 \times 10^5$ cells/flask. The cells were labelled with $^{125}$I-UDR (iodinated uridine deoxyribonucleic acid) at 0.5 microcuries/ml media (5.0 microcurie/flask). Cells were incubated for approximately 24 hours and the cell count/flask was determined to be $8.14 \times 10^5$ cell/flask. The cells from each flask were counted (gamma counter) and found to have an average of 0.24 cpm/cell.

In Vitro Attachment Assay

Platelet enhanced tumor cell attachment to plastic was tested using four conditions: tumor cell alone (Condition A), tumor cells plus washed platelets (Condition B), tumor cells plus platelet poor plasma (Condition C) and tumor cells, washed platelets and platelet poor plasma (Condition D).

Walker 256 L-Pam tumor cells obtained from culture are radiolabeled with $^{125}$I-UDR as described previously. The radiolabeled cells are removed from T-75 flasks with trypsin (2 milliliters of 0.25% trypsin and 0.01% EDTA) in MEM. After two minutes, the flasks are washed 3X with trypsin "quench," 10% fetal calf serum in MEM, to quench and remove the trypsin in order to prevent cell lysis. The tumor cells are removed from the flasks in MEM and adjusted to $2.5 \times 10^5$ cells /milliliter. One hundred microliters of the tumor cell suspension ($2.5 \times 10^4$ cells) were plated in 16 mM tissue culture wells (Costar) and overlaid with 250 microliters of Wash Solution #2 (see Platelet Prep). The cells were incubated at room temperature (approximately 22° C.) for 5 minutes. Following this incubation 10 microliters of 7.35 mg/ml CaCl$_2$ were added to the culture wells, 10 microliters of platelet poor plasma (diluted 1:32 with platelet Wash Solution #2) were added to culture wells for Conditions C and D and 250 microliters of washed platelets ($3 \times 10^8$/ml final concentration) were added to culture wells for Conditions B and D. Where appropriate, Wash Solution #2 was added to wells (Conditions A and C) so that all wells had the same final volume of solutions. The wells were incubated for one hour at 37° C. After the one hour incubation, the media containing any unattached tumor cells were removed by aspiration and then the wells were washed 2X with 1 ml of sodium phosphate buffer (PBS). The adhering cells were removed by trypsinization (as described above) and counts per wells determined using a gamma counter. Results were determined as total cpm plated per well.

Platelet enhanced tumor cell attachment to a virally transformed endothelial cell monolayer (on plastic wells) was also tested. The experimental protocal utilized was similar to that described above. The only significant difference is that in the above assay the floor of each incubation well is the plastic material of the plate, and in these assays, that plastic floor is covered with a confluent monolayer of virally transformed rat cerebral microvascular endothelial cells. The cells were prepared and plated as described in detail in *Laboratory Investigations*, Vol 46, No. 6, p534, 1982 (Diglio, C. A., Grammas, P., Giacomelli, F., and Wiener, J., Lab. Investigations Vol 46, No. 6, p554–563, 1982) and in J. Cell. Biol (Manuscript accepted 3/83) (Diglio, C., Wolfe, D. E., and Meyers, P. J. Cell. Biol. manuscript in press, 1983). Briefly, rat endothelial cells were dispersed from critical microvasculature by collagenase treatment. Migrating cells and cell proliferation are seen. Isolated cells are allowed to proliferate in culture until the expected "cobblestone" appearance characteristic of normal endothelial cells is obtained.

Cultured (subconfluent) normal endothelial cells are infected with Schmidt-Ruppin Rous Sarcoma virus-strain D (SR-RSV-D). A single transformed focus was isolated and recultured. The resulting transformed endothelial cell line was designated RCE-T1 (also known as SR-D1).

In the actual assay, the protocol for tumor cell adhesion to plastic or transformed endothelial cell are similar. The one difference between the two assays was the methodology utilized to remove the adhering tumor cells. To remove the adhering tumor cells from the endothelial cells (from the wells) the trypsin solution is allowed to remain overnight (approximately 16 hours) instead of 2 minutes. In actuality, the tumor cells are not separated from the endothelial cells, the trypsin dissolves both cell types in the wells; so the aspirated sample which is removed and counted (from each well) contains the remains of the radiolabeled tumor cells as well as the endothelial cells which coated the floor of the well.

EFFECTS OF BAY E 9736 ON TUMOR CELL GROWTH AND METASTASIS

The B16a tumor cells, obtained by the previously described procedure of tumor dispersion and tumor cell elutriation were used to test the antimetastatic effect of BAY e 9736.

Briefly, the antimetastatic effects of nimodipene (BAY e 9736) were examined in vivo and in vitro utilizing six (6) different assay systems. In vivo, the induction of lung colony formation by injection of elutriated B16a tumor cells (Example 1) and spontaneous lung colony metastasis from primary subcutaneous B16a tumors (Example 2) were examined to determine if BAY e 9736 could prevent or decrease the number of lung tumors formed. In vitro, BAY e 9736 was examined for its ability to inhibit B16a tumor cell proliferation (Example 3), $^3$H-thymidine incorporation into proliferation B16a tumor cell cultures (Example 4), Walker 256 L-Pam tumor cell adhesion to plastic wells and virally transformed endothelial cell monolayer (Example 5), and tumor cell or adenosine diphosphate (ADP) induced platelet aggregation (Example 6). Example 7 shows the effect of nifedipine (BAY a 1040) in preventing platelet aggregation.

IN VIVO METASTASIS

EXAMPLE 1

A 40 mg portion of BAY e 9736 was dissolved in 1 ml of polyethylene glycol (PEG-400). This stock solution was diluted 1:5, 1:10, 1:50 and 1:1000 with PEG-400. C56BL/6J mice weighing an average of 20 grams were injected orally with 0.1 ml of the diluted BAY e 9736 one hour before and one hour after challenge with tumor cells. One hour after the first oral administration of BAY e 9736, the mice were injected via the tail vein with a $3 \times 10^4$ B16a tumor cell suspension in 0.05 ml prepared as described previously. The control and treated mice were kept under identical conditions of temperature, feeding) photoperiod, etc. The mice were sacrificed 21 days after tail vein injection of the tumor cells and the lungs were removed, fixed in Bouin's solution and visible bilateral metastasis counted.

As demonstrated by the data represented in Table 1, BAY e 9736 is effective in reducing the number of lung colonies at all levels examined.

TABLE 1

"Experimental" Metastasis Induced by Tail Vein Injection of B16a Tumor Cells[a]

| Dose in mg/kg | % of Control[b] |
|---|---|
| 0.2 | 55 ± 5[c] |
| 4.0 | 60 ± 7 |
| 20.0 | 73 ± 13.7 |
| 40.0 | 74 ± 7.5 |

[a]$3 \times 10_4$ cells injected
[b]Mean number of metastatic lesions on lung surface for control group = 100%
[c]$\bar{x} \pm$ SEM; n = 12

EXAMPLE 2

The effect of chronic oral administration of BAY e 9736 on spontaneous lung metastasis from a primary subcutaneous B16a tumor was also determined. A 16 mg portion of BAY e 9736 was dissolved in 1 ml of PEG-400 and diluted 1:8, 1:32, 1:80, and 1:800. Syngeneic C56BL/6J mice were injected subcutaneously with $1 \times 10^5$ B16a tumor cells in 0.1 ml prepared as previously described. Starting one day post tumor injection, the mice were administered BAY e 9736 orally once a day for 27 days with 0.1 ml of the diluted BAY e 9736. The control and treated mice were housed under identical conditions of temperature, feeding and photoperiod, etc. The mice were sacrificed 28 days after the injection of tumor cells and the lungs were removed in Bouin's solution and visible bilateral metastasis counted. As shown by the data in Table 2, BAY e 9736, at all doses tested, is effective in decreasing the number of spontaneous metastasis as compared to the control mice.

TABLE 2

"Spontaneous" Metastasis from an In Vivo subcutaneous Implant of B16a Tumor Cells

| Dose in mg/kg[a] | % of Control[b] |
|---|---|
| 0.1 | 68 ± 14[c] |
| 1.0 | 45 ± 9 |
| 2.5 | 33 ± 22 |
| 10.0 | 28 ± 7 |
| 80.0 | 19 ± 6 |

[a]Chronic administration of BAY e 9736 put orally once daily
[b]Mean number of pulmonary metastatis in control group mice = 100%
[c]$\bar{x} \pm$ SEM; N = 10

IN VITRO TUMOR CELL PROLIFERATION

EXAMPLE 3

A 40 mg aliquot of BAY e 9736 was dissolved in 1 milliliter dimethyl sulfoxide (DMSO). Aliquots of this 40 mg/ml stock were diluted with DMSO to final concentrations of 20 and 10 mg/ml. At day two and each successive day, 10 microliter aliquots of 40, 20, and 10 mg/ml BAY e 9736 were added once a day to the new media of flasks containing proliferating B16a tumor cells as previously described. As depicted in Table 3, BAY e 9736 inhibits tumor cell proliferation at 40, 20 and 10 micrograms/ml, final concentration.

TABLE 3

In Vitro Proliferation of B16a Tumor Cells[a]

| Dose of BAY e 9736 | % of Control Tumor Cell Number |
| --- | --- |
| Control | $100 \pm 7^b$ |
| Control + DMSO | $100 \pm 4$ |
| .04 mg/ml | $14 \pm 3$ |
| .02 mg/ml | $25 \pm 5$ |
| .01 mg/ml | $50 \pm 5$ |

[a] Media changed once daily; drug and DMSO control, DMSO re-added with new media
[b] $\bar{x} \pm$ SEM; n = 4

EXAMPLE 4

A variation of the previously described experiment was used to determine the effects of BAY e 9736 on a different parameter of tumor cell proliferation, the replication of deoxyribonucleic acid (DNA) as measured by the incorporation of $^3$H-thymidine into tumor cell DNA. B16a tumor cells were grown in T-75 flasks and removed using trypsin, as previously described for Walker 256 L-Pam tumor cells. The B16a cells are quenched, washed, and resuspended in media (MEM+10% fetal calf serum, FCS) to a concentration of $1 \times 10^5$ cells/ml. One milliliter of tumor cells are placed into 5 ml plastic incubation tubes, and five microliters of media, dilutant, or dilutant containing 8, 4, or 2 milligram/ml BAY e 9736 are added to appropriate tubes. The assay was run, terminated, and the B16a tumor cell DNA extracted and counted as previously described. As represented in TABLE 4, all concentrations of BAY e 9736 inhibited the incorporation of $^3$H-thymidine into the tumor cell DNA.

TABLE 4

$^3$H—Thymidine[a] Incorporation[b] into Cultured B16a Tumor Cells

| Dose of BAY e 9736 | % of Control Tumor Cell Incorporation |
| --- | --- |
| Control | $100 \pm 8^c$ |
| Control + DMSO | $100 \pm 2.5^c$ |
| .04 mg/ml | $38 \pm 4$ |
| .02 mg/ml | $56 \pm 3.5$ |
| .01 mg/ml | $77 \pm 2.5$ |

[a] 1 microcurie/ml $^3$H—thymidine; 15 minute preincubation with BAY e 9736
[b] 1 hour incorporation in the presence of drug
[c] $\bar{x} \pm$ SEM; n = 4

IN VITRO TUMOR CELL ADHESION

EXAMPLE 5

The effect of BAY e 9736 on Walker 256 L-Pam tumor cell adhesion to plastic wells of a virally transformed endothelial cell confluent monolayer was determined by pretreating monodispersed Walker 256 L-Pam tumor cells with BAY e 9736 dissolved in DMSO prior to plating the cells. Except for the pretreatment, plastic adhesion studies were performed as previously described in the literature. A 8 mg sample of BAY e 9736 was dissolved in 1 ml of DMSO. Five microliters of the 8 mg/ml BAY e 9736 was added to each 1 ml of tumor cells. Thirty minutes preincubation with 40 microgram/ml (0.04 mg/ml; final concentration) BAY e 9736 decreased the percent of cells adhering to the plastic wells as well as the endothelial cell monolayer. As represented in Tables 5a and 5b, the inhibitory effects of BAY e 9736 were significant in all groups tested whether the substrate was the plastic floor of the incubation wells or the confluent monolayer of transformed endothelial cells.

TABLE 5a

Tumor Cell[a] Attachment to Plastic

| BAY e 9736 (0.04 mg/ml) | % Inhibition vs control[d] |
| --- | --- |
| A | $72^c \pm 5.9$ |
| B[b] | $50 \pm 8.2$ |
| C[c] | $44 \pm 9.2$ |
| D[b] | $40 \pm 7.5$ |

A = t.c., alone
B = t.c. + platelets
C = t.c. + PPP
D = t.c. + PPP + platelets
[a] $2.5 \times 10^4$ tumor cells/well
[b] $3 \times 10^8$ platelets/well
[c] 10 microliters platelet poor plasma (PPP) diluted 1:32 with media
[d] Control = 100% = that number of tumor cells (measured as cpm) adhering after one (1) hour of plating time. Each condition A, B, C and D was calculated separately and standardized as 100%.

TABLE 5b

Tumor Cell[a] Attachment to Endothelial Cells[f]

| BAY e 9736 (0.04 mg/ml) | % Inhibition vs Control[d] |
| --- | --- |
| A | $50^e \pm 9.5$ |
| B[b] | $65 \pm 7.8$ |
| C[c] | $60 \pm 5.0$ |
| D[b] | $53 \pm 5.5$ |

A = t.c., alone
B = t.c. + platelets
C = t.c. + PPP
D = t.c. + PPP + platelets
[a] $2.5 \times 10^4$ tumor cells/well
[b] $3 \times 10^8$ platelets/well
[c] 10 microliters platelet poor plasma (PPP) diluted 1:32 with media
[d] Control = 100% = total number of tumor cells (measured as cpm) adhering after one hour plating time. Each condition, A, B, C, and D was calculated separately and standardized as 100%.
[e] $\bar{x} \pm$ SEM; n = 4
[f] Endothelial cell line RCE-T1

IN VITRO TUMOR CELL INDUCED PLATELET AGGREGATION

EXAMPLE 6

A 20 milligram sample of BAY e 9736 was dissolved in 1 ml of polyethylene glycol (PEG-400) and serially diluted with PEG-400 to 2, 0.2 and 0.02 mg/ml concentrations using PEG-400. Tumor cell induced platelet aggregation (TCIPA) studies were performed as described previously. The effect of BAY e 9736 on TCIPA was determined by the mixing of 2 or 5 microliter aliquots of 20, 2, 0.2 or 0.02 mg/ml BAY e 9736 and the platelet rich plasma (PRP) for approximately 3 minutes prior to the addition of tumor cells. Table 6 represents the results of this series of experiments. BAY e 9736 does inhibit TCIPA at dose ranges from 400 micrograms/ml to 0.4 micrograms/ml. The greatest inhibition was observed at the higher concentrations of BAY e 9736.

Adenosine diphosphate (ADP) was prepared as a 1 mM solution (in distilled water). A 25 microliter aliquot was added to control and BAY e 9736 treated cuvettes containing PRP. The ADP concentration used induces rapid, monophasic platelet aggregation. The higher concentrations of BAY e 9736 are able to significantly inhibit this aggregation.

TABLE 6

Aggregometry Data
% Inhibition of Tumor Cell and ADP Induced Platelet[a] Aggregation

| BAY e 9736 (Final Concentration) | Tumor Cells[b] | 0.1 mM ADP[c] |
|---|---|---|
| 0.4 mg/ml | 85 ± 9.6[d] | 69 ± 7.5[d] |
| 0.15 mg/ml | 67 ± 8.5 | 58 ± 11 |
| 0.04 mg/ml | 55 ± 7.7 | 31 ± 6.2 |
| 0.015 mg/ml | 32 ± 3.5 | No effect to 12% |
| 0.004 mg/ml | 19 ± 5.9 | No effect |
| 0.0015 mg/ml | 12 ± 4.1 | No effect |
| 0.004 mg/ml | No effect | No effect |
| 0.00015 mg/ml | No effect | |

[a]250 microliters PRP at $3 \times 10^8$ platelets/ml in all cuvettes
[b]20 microliters tumor cells at $25 \times 10^6$ cells/ml
[c]25 microliters $10^{-3}$ M ADP
[d]$\bar{x} \pm$ SEM; n = 3

EXAMPLE 7

The calcium channel blocker nifedipine was tested for its ability to inhibit tumor cell induced platelet aggregation (TCIPA). Nifedipine (20 mg) was dissolved in one milliliter of abolute ethanol:PEG-400 (1:1), and then diluted 1:10 with the same ethanol:PEG-400 mixture. The protocol for the aggregation studies was identical to that explained in the preceding example, except that the tumor line used in this study was Lewis Lung Carcinoma (3LL) instead of the B16 amelanotic melanoma (B16a). The control cuvette light transmittance was standardized as 100% aggregation. A 2.0 ul aliquot of control dilutant or dilutant containing 20 or 2 mg/ml nifedipine was added to the control and experimental cuvettes, respectively, immediately followed by the addition of 250 microliters of PRP. The mixtures were allowed to equilibrate in the aggregometer for approximately 3 minutes, after which a 20 microliter aliquot of 3LL cells was added to each cuvette to induce platelet aggregation. The results in Table 7 indicate that nifedipine can inhibit TCIPA in a dose dependent fashion. Furthermore, these results suggest that the inhibitory actions of nimodipine of B16a TCIPA are a general phenomena and are not restricted to nimodipine or the B16a tumor cell line.

TABLE 7

| NIFEDIPINE | INHIBITION OF CONTROL TCIPA |
|---|---|
| 0.15 mg/ml | 42% ± 2% |
| 0.015 mg/ml | 22% ± 3% |

NIFEDIPINE EFFECTS ON $^3$H-THYMIDINE INCORPORATION INTO B16a TUMOR CELLS (COMPARISON VS. NIMODIPINE)

Protocol same as previously described except nifedipine (40 mg) is first dissolved in absolute ethanol (0.5 ml) and then diluted with PEG-400 (1.5 ml) to a final concentration of 20 mg/ml. One microliter of the 20 mg/ml nifedipine solution was added to one ml of B16a tumor cells (for final concentration of 20 micrograms/ml). Nimodipine was dissolved as previously described. The results are shown in Table 8.

TABLE 8

| | % $^3$H—Thymidine Incorporation % of Control |
|---|---|
| Control | 100% ± 6% |
| Control (+ diluent) | 100% ± 7% |
| 20 microgram/ml nimodipine | 7% ± 1% |
| 20 microgram/ml nimodipine | 22% ± 3% |
| 20 microgram/ml nifedipine | 22% ± 3% |

Numerous obvious variations of the present invention will occur to those skilled in the art. It is intended to include these variations within the scope of the present invention.

We claim:

1. A method for reducing interaction between blood platelets and malignant tumors present in the blood and resulting attachment of the tumors with the platelets in blood vessels in a mammal which comprises:
   administering to a mammal in need thereof an effective amount of a calcium channel blocker compound selected from the group consisting of phenylalkyamines, benzothiapenes, diphenylalkylamines and 1,4-dihydropyridines which is substituted in the 4-position which reduces the interaction between the platelets and the tumors and resulting attachment of the tumors with the platelets in the blood vessels without treating the tumors to thereby interfere with the metastatic cascade in the mammal and wherein in vitro the calcium channel blocker compounds prevent aggregation of tumor cells and platelets.

2. A method as claimed in claim 1 wherein the tumor is produced by B-16 amelanotic melanoma in mice as the mammal.

3. The method of claim 1 wherein the compound is a 1,4-dihydropyridine which is substituted in the 4-position.

4. The method of claim 1 wherein the compound is 1,4-dihydro-2-,6-dimethyl-4-(3'-nitrophenyl)-pyridine-3-(low er alkyl ester)-5-(lower alkyl ester), wherein lower alkyl contains between 1 to 6 carbon atoms.

5. The method of claim 1 wherein the compound is nifedipine.

6. The method of claim 1 wherein the calcium channel blocker compound is nimodipine.

7. The method of claim 1 wherein the administration is oral.

* * * * *

UNITED STATES PATENT AND TRADEMARK OFFICE
CERTIFICATE OF CORRECTION

PATENT NO. : 4,690,935
DATED : September 1, 1987
INVENTOR(S) : John D. Taylor and Kenneth V. Honn Page 1 of 2

It is certified that error appears in the above-identified patent and that said Letters Patent are hereby corrected as shown below:

Column 1, line 14 "nifedepine" should be --nifedipine".

Column 2, line 34 "chim." should be --chem.--.

Column 3, line 50 "infraction" should be --infarction--.

Column 6, line 59 "pices" should be --pieces--.

Column 8, line 62 "contamination Typical" should read --contamination. Typical--.

Column 11, line 5 "protocal" should be --protocol--.

Column 11, line 61 "proliferation" should be --proliferating--.

Column 12, line 16 "feeding)" should be --feeding,--.

Column 12, line 32 "3 x 10$_4$" should be --3 x 10$^4$--.

Column 13, line 39 "dilutant" (both occurrences) should be --diluent--.

Column 13, line 64 "wells of" should be --wells or--.

Column 14, line 1 "A 8" should be --An 8".

Column 14, line 17 (Table 5a) the "e" should be deleted.

Column 15, line 31 "abolute" should be --absolute--.

UNITED STATES PATENT AND TRADEMARK OFFICE
CERTIFICATE OF CORRECTION

PATENT NO. : 4,690,935
DATED : September 1, 1987
INVENTOR(S) : John D. Taylor and Kenneth V. Honn It is certified that error appears in the above-identified patent and that said Letters Patent are hereby corrected as shown below:

Column 15, line 41 "dilutant" (both occurrences) should be --diluent--.

Column 15, line 52 "of B16a" should be --on B16a--.

Column 16, line 53 "low er" should be --lower--.

Signed and Sealed this

Second Day of February, 1988

Attest:

DONALD J. QUIGG

Attesting Officer          Commissioner of Patents and Trademarks